United States Patent [19]

Bonne

[11] Patent Number: 5,055,690

[45] Date of Patent: Oct. 8, 1991

[54] METHOD OF ELIMINATING WATER VAPOR INTERFERENCE IN DETECTING GASES

[75] Inventor: Ulrich Bonne, Hopkins, Minn.

[73] Assignee: Gas Research Institute, Chicago, Ill.

[21] Appl. No.: 458,244

[22] Filed: Dec. 28, 1989

Related U.S. Application Data

[63] Continuation-in-part of Ser. No. 308,469, Feb. 10, 1989, Pat. No. 4,958,076.

[51] Int. Cl.$^5$ ............................................. G01N 21/61
[52] U.S. Cl. .................................... 250/343; 250/334
[58] Field of Search ......................... 250/343, 339, 345

[56] References Cited

U.S. PATENT DOCUMENTS

| | | |
|---|---|---|
| 2,741,703 | 4/1956 | Munday . |
| 3,551,678 | 12/1970 | Michell . |
| 3,678,262 | 7/1972 | Hermann . |
| 3,743,426 | 7/1973 | Steinberg . |
| 3,790,797 | 2/1974 | Sternberg et al. .................. 250/345 |
| 3,832,548 | 8/1974 | Wallack ............................... 250/343 |
| 3,893,770 | 7/1975 | Takami et al. ..................... 250/339 |
| 3,897,154 | 7/1975 | Hawes ................................. 250/345 |
| 3,968,367 | 7/1976 | Berg .................................... 250/339 |
| 4,054,384 | 10/1977 | Hawes ..................................... 356/51 |
| 4,273,450 | 6/1981 | Watanabe et al. ................... 356/433 |
| 4,297,579 | 10/1981 | Spaeth ................................... 25/343 |
| 4,520,265 | 5/1985 | Griggs et al. ...................... 250/339 |
| 4,543,481 | 9/1985 | Zwick .................................. 250/339 |
| 4,560,873 | 12/1985 | McGowan et al. ................. 250/339 |
| 4,567,366 | 1/1986 | Shinohara ........................... 259/339 |
| 4,707,603 | 11/1987 | Miemelä et al. .................... 250/343 |

FOREIGN PATENT DOCUMENTS 1000070 11/1976 Canada .............................. 250/343

Primary Examiner—Carolyn E. Fields
Attorney, Agent, or Firm—Thomas W. Speckman; Douglas H. Pauley

[57] ABSTRACT

A method of eliminating additional absorption caused by water vapor in detecting gases wherein absorption of infrared light is used to determine measured abosrption signals and interference absorption signals. The method of eliminating water vapor absorption comprises the steps of emitting infrared light from a light source into an optical cell, and admitting sample gas into the optical cell. The infrared light is passed through the optical cell to a chopper wheel which positions at least two band pass filters and the filtered light emitted from the band pass filters is detected by an infrared radiation detector. The interference caused by water vapor absorption at a measurement channel is subtracted and thus, a true measurement channel which is free of any interference caused by water vapor absorption is produced. The true measurement channel is used to positvely and accurately identify the gas. The method of this invention may also be used to eliminate interference around more than one measurement channel.

15 Claims, 3 Drawing Sheets

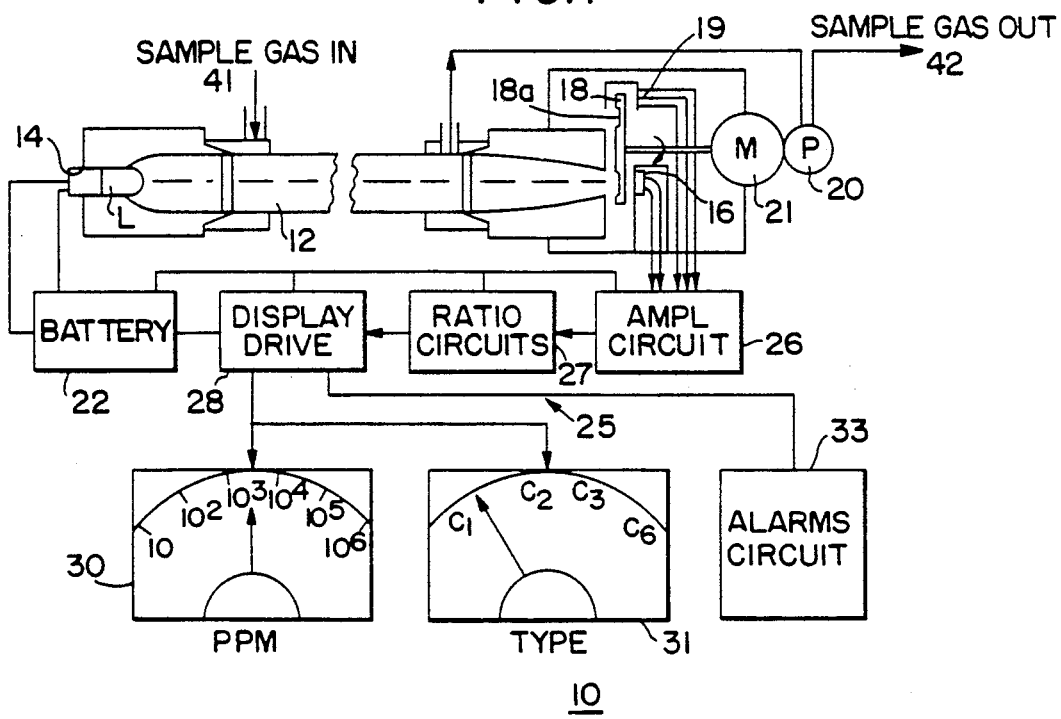
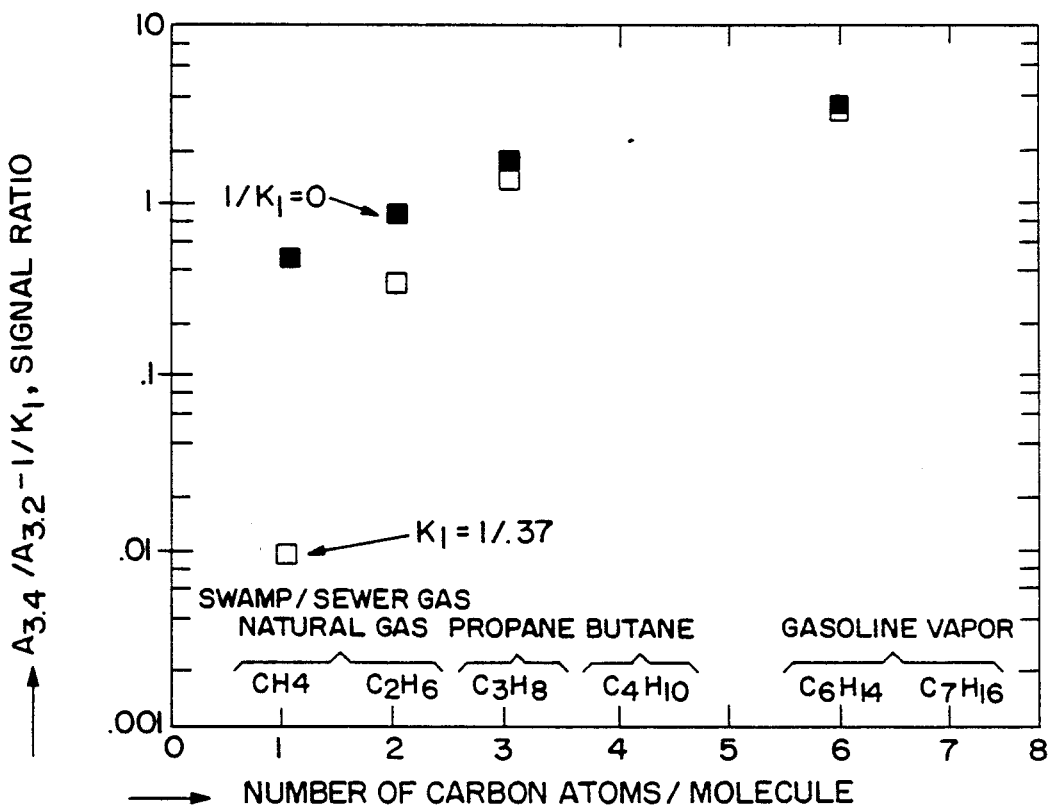

METHOD OF ELIMINATING WATER VAPOR INTERFERENCE IN DETECTING GASES

BACKGROUND OF THE INVENTION

1. Field of the Invention

This invention relates to a method of eliminating water vapor interference in detecting gases wherein absorption of infrared light is used to determine measured absorption and interference absorption.

2. Description of Prior Art

Utilities which distribute natural gas require reliable, portable gas-leak detectors for use in maintenance of gas supply lines. Existing natural gas detectors are either costly, sensitive and non-selective or low cost, insensitive and non-selective. Non-selective gas detectors respond to any combustible gas. Selective gas detectors are specific to hydrocarbon gases. The two most presently used detectors are based on hydrogen flame ionization and on hot wire catalysis which cannot distinguish among different types of hydrocarbons. However, it is necessary to distinguish among different types of hydrocarbons in order to distinguish a pipeline gas from gasoline vapors or sewer or swamp gas and to reduce leak surveyor time wasted on false alarms. Ethane content, if measurable, provides a good means to discriminate between pipeline gas and interfering sewer or swamp gases because the latter contain practically no ethane, while pipeline gas does, in varying degrees. Gasoline vapors and propane (LP gas) can also generate a false alarm with conventional instruments. However, their infrared absorption is shifted relative to that of methane, as will be described later, it is the basis for this invention to eliminate interference caused by water vapor and to eliminate sending false alarms.

Many methods have been developed to eliminate undesirable interferences in gas sensors. However, existing infrared absorption band gas detectors are unable to eliminate interference caused by water vapor in the gas being detected. This water vapor interference can be caused by naturally occurring humidity in the air or the environment in which the detector is being used.

U.S. Pat. No. 4,507,558 discloses a selective detector for natural gas which discriminates between low concentrations of natural gas and other methane sources by measuring the characteristics of the methane/ethane ratio of natural gas as well as by using a combustible gas sensor. The operation of this detector is based on infrared light absorption of methane and ethane in combination with another non-specific combustible gas detector whereby the detector has the ability to detect non-specifically, the presence of a combustible gas, and to define the nature of the combustible gas. Thus, this natural gas detector utilizes two types of detection including non-dispersive infrared detectors and a non-specific combustible detector such as a hot-wire catalytic combustible detector. The detector determines concentration of the other gas by using absorption cells placed in front of the detectors. The detector includes a light emitting diode which issues light centered around 3.32 microns and a reference light source which emits light at a wavelength outside of this band. Although this arrangement permits distinguishing among different types of hydrocarbons, the requirement for a hot-wire catalytic combustible detector adds cost and complexity to the device and increases power consumption.

U.S. Pat. No. 3,893,770 teaches a multi-channel gas analyzer which decreases interferences among the absorption spectra for component gases of mixed gases. The '770 patent discloses an apparatus which uses a spectrophotometer to detect an absorption spectra for each of three types of gases and further uses a single measurement device to determine the concentrations of the three types of component gases. A dispersive spectrometer is used to obtain absorption spectra of specific wavelength ranges corresponding to the component gases which make the interferences between the component gases irreversible. The absorption spectra are converted to electrical signals and the concentrations of the component gases are measured by compensating for irreversible interferences by means of function generations and arithmetic units each of the numbers of which are equal to that of the irreversible interferences.

U.S. Pat. No. 4,054,384 discloses an infrared radiation source which passes infrared radiation through a cell to a conventional Michelson-type analyzing interferometer and the resultant radiation proceeds to a detector, which emits an electrical signal. The electrical signal is split into two signals, one signal passes through a time delay device in route to an input amplifier, and the other signal passes directly to the input amplifier. The differential amplifier operates in conjunction with a delay device to provide autocancellation of signal components due to contaminants in the sample gas stream.

U.S. Pat. No. 3,897,154 discloses a method of determining unknown constituents and measuring constituent concentrations in a fluid while a contaminant or extraneous constituent of the fluid interferes with monitoring the constituents sought. The '154 patent teaches that the unknown constituents, of the fluid, flow in a path so as to influence the time delay between the arrival of each sample constituent at two stations. The '154 patent teaches a substantial delay, compared with the effective residence time of the stream at the last station, the station which the sample arrives at first. The two samples from the respective measurement stations may be compared with each other and interrupted in various ways, including but not limited to subtraction of one signal from the other. Thus the two signals may provide contaminant-effect autocancellation and may be equal.

U.S. Pat. No. 4,273,450 discloses determining characteristics of unknown samples with a photoacoustic spectrometer. An electrical signal obtained from an unknown-sample unit is cross-correlated with an electrical signal from a reference-sample unit to produce a third signal which is used to identify the unknown sample.

It would be highly desirable to have a natural gas detector which can positively distinguish among different types of hydrocarbons by eliminating absorption caused by water vapor, and can provide information to the operator on the amount and type of combustible gases in the environment.

SUMMARY OF THE INVENTION

An object of this invention is to provide an accurate, inexpensive method for detecting gases which eliminates additional absorption caused by water vapor.

Another object of the invention is to provide a method for detecting gases which eliminates water vapor absorption caused at a specific measurement channel, thus providing an accurate indication of the gas being detected.

A further object of this invention is to provide a natural gas detector which entirely eliminates water vapor absorption by subtracting a measurement interference absorption signal from a measurement absorption signal to determine a true measurement channel.

A still further object of this invention is to provide a method for detecting gases including eliminating water vapor absorption around at least two measurement channels.

These and other objects of this invention are achieved by providing a method of eliminating water vapor absorption, preferably in a selective gas detecting apparatus, by measuring interference absorption of infrared radiation. In one preferred embodiment of this invention, a method of eliminating water vapor absorption begins with emitting infrared light from an infrared radiation source into an optical cell. A gas is admitted or introduced into the optical cell. At least two band pass filters are positioned within a rotating chopper wheel. Infrared radiation is passed through the optical cell and the band pass filters. Filtered light emitted from the band pass filters is detected and used to determine a water vapor absorption signal in a measurement channel. The water vapor absorption signal is subtracted from a measurement absorption signal of the measurement channel to eliminate the water vapor absorption from the measurement channel.

The invention comprises certain novel methods and details hereinafter fully described, illustrated in the accompanying drawings, and particularly pointed out in the appended claims, it being understood that various changes in the details may be made without departing from the spirit, or sacrificing any of the advantages of the present invention.

DESCRIPTION OF THE DRAWINGS

For the purpose of facilitating and understanding the invention, illustrated in the accompanying drawings a preferred embodiment thereof, from an inspection of which, when considered in connection with the following description, the invention, its construction and operation, and many of its advantages will be readily understood and appreciated.

FIG. 1 is a simplified schematic representation of a method for detecting gases which includes eliminating interference caused by water vapor;

FIG. 2 is a graphic representation of the relationship between the signal output of the type or average type of the gas detector display versus different but individual types of hydrocarbons in a gas sample;

DESCRIPTION OF A PREFERRED EMBODIMENT

Figure 4:
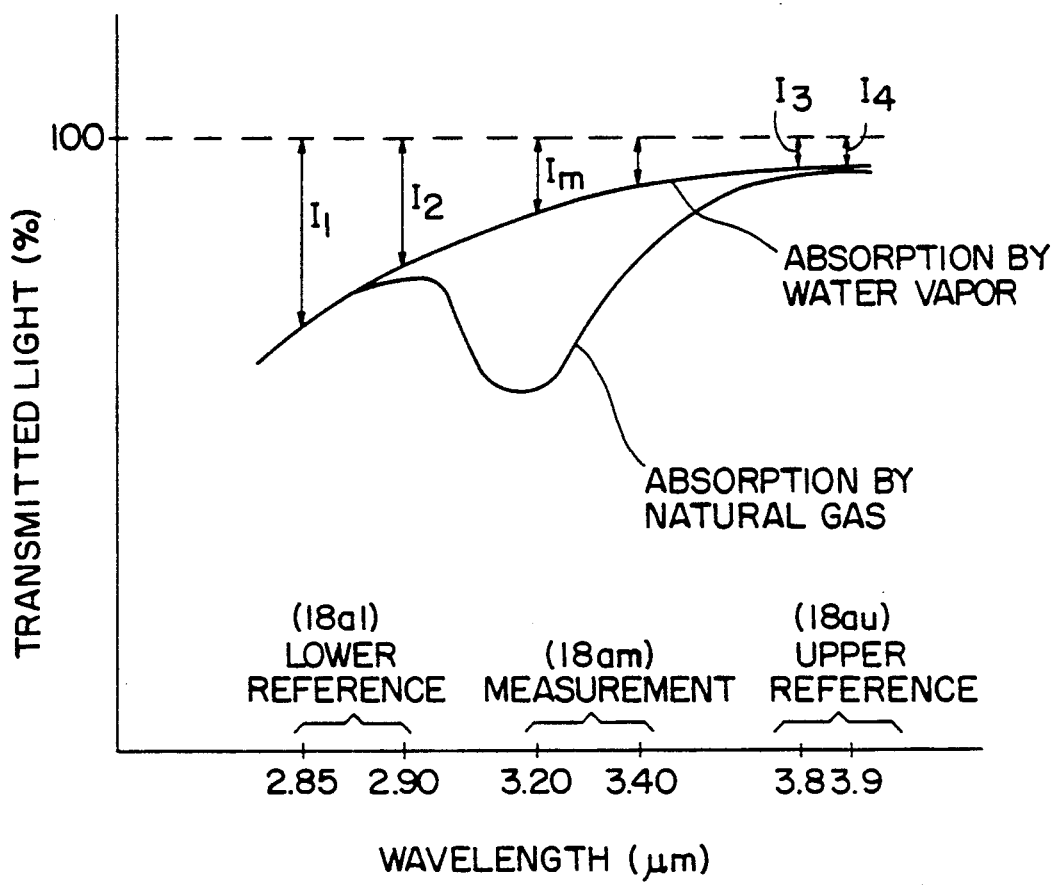
FIG. 4 is a graph showing the wavelength of the reference channels and measurement channel along the abscissa and the intensity along the ordinate.

Water vapor causes false or inaccurate readings in gas detecting apparatuses that measure the absorption of infrared light passed through a measured gas sample. Referring to FIG. 4, the arrows in the graph represent interference caused by water vapor. As shown by the arrows in the graph of FIG. 4, water vapor causes additional absorption which creates an inaccurate signal.

The arrow identified as Im represent measured water vapor interference. The additional absorption caused by water vapor, for example as shown in FIG. 4, increases as the wavelength of the reference channel or measurement channel increases. If the operator of a detector could positively identify the gas by eliminating water vapor absorption, guesswork and other uncertainties in the field could be eliminated. For example, natural gas has a wavelength of approximately 3.2 microns and an indicated absorption reading at 3.2 microns would confirm the presence of natural gas. However, an indicated absorption reading of 3.29 microns will not confirm whether the gas being detected is natural gas distorted by water vapor absorption or some other type of gas. The present invention eliminates the water vapor absorption and provides an accurate method for determining a true measurement channel. In one embodiment of this invention, the measurement channel or channels will be fixed and each corresponding reference channel wavelength can vary within certain ranges.

In a preferred embodiment of this invention, interference absorptions of reference channels are combined so that a resulting water vapor absorption signal is equal to the absorption caused by water vapor in a measurement channel. Then using signal processing, the water vapor absorption signal is subtracted from the measurement intensity and thus eliminates the absorption caused by water vapor and produces a true measurement channel.

Figure 5:
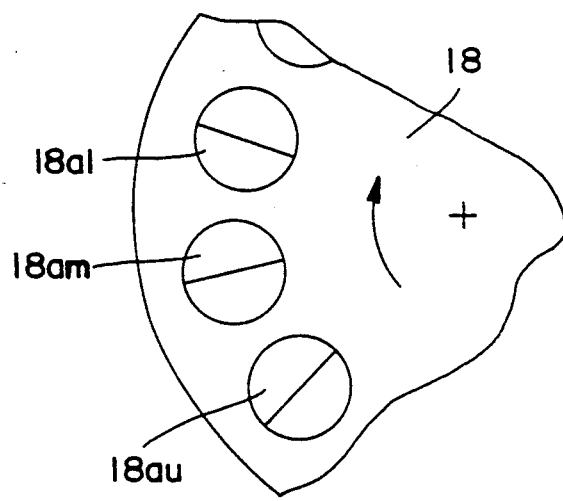
FIG. 5 is a partial view of a chopper wheel positioning a lower reference channel band pass filter, a measurement channel band pass filter and an upper reference channel band pass filter.

Referring to FIG. 1, the operation of natural gas detecting apparatus 10 provided by the present invention is based upon the absorption of infrared light by a gas sample, as the gas sample is pumped or drawn through a gas sample chamber which is defined as optical cell 12. Optical cell 12 may also be referred to as an absorption tube. Natural gas detecting apparatus 10 includes a gas detection arrangement which determines gas concentration, for example the total concentration of hydrocarbons in the gas sample, and the gas type, such as swamp or sewer gas, natural gas, propane, gasoline vapors and others. The gas sample is analyzed using optical cell 12 which defines a gas sample optical path length, an infrared radiation source 14 and an infrared radiation detector 16. At least two band pass filters, generally denoted as element 18a, are interposed therebetween. As illustrated in FIG. 1, means for positioning at least two band pass filters 18a comprise a chopper wheel 18. In a preferred embodiment, rotating chopper wheel 18 carries at least two band pass filters 18a. FIG. 6 illustrates a section of chopper wheel 18 having three band pass filters 18. FIG. 5 shows lower band pass filter 18al, a measurement channel band pass filter 18am, and upper band pass filter 18au. In FIG. 5, the area of the band pass filters 18al, 18am and 18au is circular. It is not necessary for band pass filters 18a to have any particular spacing on chopper wheel 18, as long as the detector is programmed to know which band pass filter 18a is emitting light.

It is apparent that the positioning of band pass filters 18a need not be confined to a rotating disc or wheel. The means for positioning may, for example, be a device having linear positioning or other suitable positioning of band pass filters 18a wherein the infrared light is passed through the optical cell then to band pass filter 18a. The area that the band pass filters 18a occupy in chopper wheel 18 may be circular or any other suitable geometrical shape. When using chopper wheel 18 with circular band pass filters 18a, each circular area may be divided into two halves, as shown in FIG. 5, or other multiple sections. Each of the two halves may be used to position two or more band pass filters 18a.

Referring to FIG. 1, pump 20 preferably moves the sample gas through optical cell 12 at the rate of about two liters per minute. In one preferred embodiment, pump 20 is driven by a motor 21 which also rotates chopper wheel 18. The use of a conventional motor 21 to rotate chopper wheel 18 and pump 20 reduces power requirements for natural gas detecting apparatus 10, particularly a portable natural gas detecting apparatus 10. According to a preferred embodiment, natural gas detecting apparatus 10 is energized by battery 22 which may comprise one 12 volt, or two 5 volt, rechargeable nickel cadmium battery or the like that provides power for long hours of operation. In this embodiment, natural gas detecting apparatus 10 consumes only 4 watts, including the one watt pump 20.

Infrared radiation detector 16 detects infrared radiation in selected bands and produces electrical measurement signals at the wavelengths absorbed by the gases in the sample, and thus the measurement signals are indicative of the gases which comprise the sample. Timing signals for use in processing the measurement signals are generated by a non-contacting type pickup 19 which may be an optical, magnetic or capacitive type device.

The signals produced by infrared radiation detector 16 and pickup 19 are applied to processing circuits, generally indicated by element number 25. Processing circuits 25 include an amplifier and demodulating circuit 26, ratio circuits 27, and a display drive circuit 28 which provides drive signals for a pair of analog meters 30 and 32. An alarm circuit 33 provides an alarm indication whenever a preselected gas concentration level is reached or exceeded.

In a preferred embodiment, optical cell 12 has a circular cross-sectional area; it is apparent that other suitable cross-sectional areas can be used. Optical cell 12 is approximately 25-100 centimeters in length, preferably approximately 50 cm. The diameter of a circular optical cell 12 is preferably approximately 0.25 cm and may be as large as 8 cm or greater. The inner surface of optical cell 12 is reflective and has a gold coating to internally reflect the radiation directed thereto. Optical cell 12 receives a sample of a gas to be analyzed by pump 20 which draws the gas sample into optical cell 12 through an inlet 41 and exhausts the gas sample from optical cell 12 through an outlet 42. Optical cell 12 is also generally opaque to outside light other than infrared radiation source 14. The light from infrared radiation source 14 is optically collimated by a reflector (not shown), channeled through the internally reflecting optical cell 12 and is concentrated by a parabolic, non-imaging concentrator 44 located forward of radiation detector 16. Optical cell 12 has windows (not shown) on each end which are sealed to the parabolic surfaces of the reflectors 43 and 44. The gas sample is applied to optical cell 12 by a detector sample wand (not shown) which is attached to inlet 41 of optical cell 12. A suitable outlet hose (not shown) is connected between outlet 42 and pump 20.

In a preferred embodiment, infrared radiation source 14 comprises a tungsten sub-miniature light bulb. To increase sensitivity, the output of infrared radiation source 14 is mechanically chopped at a 50 to 1000 Hz, preferably 300 Hz, rate by the action of chopper wheel 18. It should be also understood that any type of light source emitting infrared radiation may also be used in the present invention.

Figure 3:
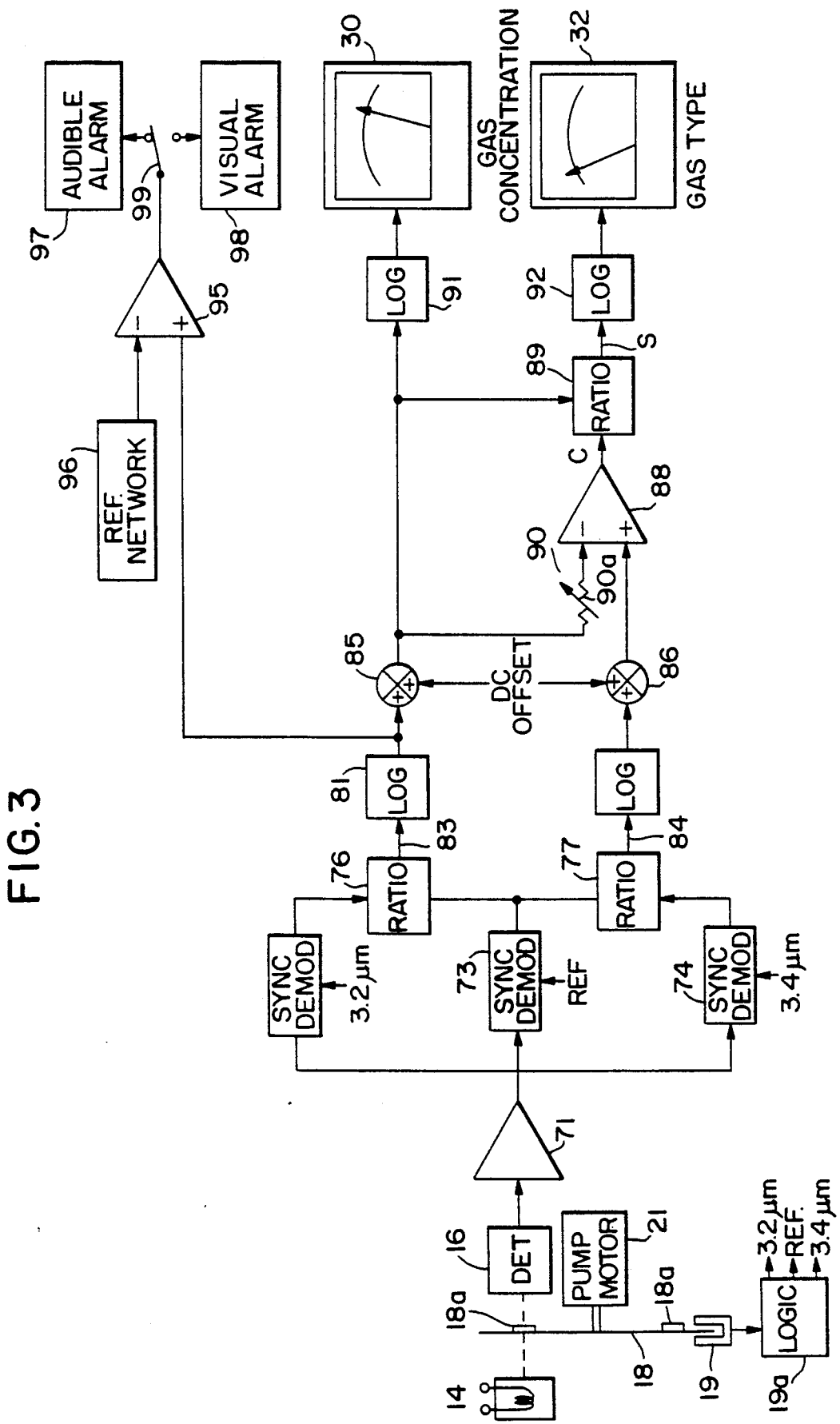
FIG. 3 is a block diagram of a preferred embodiment of a natural gas detector system, according to this invention.

Referring to FIGS. 1 and 3, chopper wheel 18 is driven by motor 21 which can also be used to operate pump 20. Chopper wheel 18, may for example, comprise a one inch diameter disc with the separation between an optical axis and the chopper wheel axis being one-quarter inch in one embodiment. According to a preferred embodiment, chopper wheel 18 carries a plurality of band pass filters 18a including a measurement channel filter 18am at 3.2 microns, a lower reference channel filter 18al in a range from about 2.8 to about 3.0 microns, and an upper reference channel filter 18au in a range from about 3.8 to about 4.1 microns. Non-contacting pickup 19 generates gating or phase timing signals relative to these three channels for demodulating the detection signals.

In accordance with a preferred embodiment of a process of the present invention, the absorption caused by water vapor can be eliminated by first admitting a sample gas into optical cell 12. An infrared radiation source 14 is passed through the sample gas. At least two band pass filters 18a, preferably more, are positioned between infrared radiation source 14 and infrared radiation detector 16. The at least two band pass filters 18a comprise at least one lower reference channel filter 18al or at least one upper reference channel filter, preferably both, and at least one measurement channel filter 18am. Once the water vapor absorption signal is detected, it is subtracted from a measurement signal of the measurement channel to eliminate the water vapor absorption from the measurement channel.

In a preferred embodiment of this invention, the absorption caused by water vapor around a measurement channel can be eliminated by using at least three band pass filters 18a. In this embodiment, the absorption of a lower reference channel is measured. When detecting natural gas for example, the lower reference channel preferably has a wavelength in the range of about 2.8 to 3.1 microns. By measuring the actual absorption of the known lower reference channel, a lower interference absorption signal may be determined. The lower interference absorption signal is determined by comparing the measured absorption of the lower reference channel to a known or stored intensity of a lower reference channel. In such known or stored intensity for the lower reference channel, it is known that there is no absorption due to water vapor. A measurement absorption of the measurement channel is measured. The actual absorption of an upper reference channel is measured. For detecting natural gas, the upper reference channel preferably has a wavelength of about 3.8 to 4.1 microns. An upper channel absorption signal for the known upper reference channel is determined by comparing the measured absorption of the upper reference channel to a known or stored absorption of the upper reference channel. In such known or stored absorption for the upper reference channel, it is known that there is no absorption due to water vapor.

A measurement absorption signal is extrapolated from a linear function or relationship between the lower channel absorption signal and the upper channel absorption signal. The measurement interference absorption signal is equal to the absorption caused by water vapor at the measurement channel. Specifically for natural gas detection, the measurement channel will be at approximately 3.2 microns. By subtracting the measurement interference absorption signal from the actual measurement absorption, a true measurement channel signal is produced. Hence, the sample gas can be ascertained as natural gas, for example, and less time will be spent responding to false control alarms caused by water vapor absorption. It is apparent that other specific wavelengths can be used to detect gases other than natural gas.

In accordance with another preferred embodiment of this invention, the absorption caused by water vapor can be eliminated from two measurement channels. In this embodiment, if the presence of natural gas, which consists primarily of methane, is to be determined, the first measurement channel will be selected at approximately 3.2 microns, and the second measurement channel for determining the presence of a second gas, for example ethane, will be selected at approximately 3.4 microns. In this particular embodiment, the absorptions of a plurality of first lower reference channels are measured. The plurality of first lower reference channels have wavelengths in a range from about 2.8 to 3.1 microns. The actual absorptions of a plurality of a first upper reference channels are measured. The plurality of first upper reference channels have known wavelengths in a range of about 3.8 to 4.1 microns. First lower interference absorption signals of the plurality of first lower reference channels are determined and first upper interference absorption signals of the plurality of first upper reference channels are determined. Absorptions of a plurality of second lower reference channels are measured. Absorptions of a plurality of second upper reference channels are measured. The plurality of second lower reference channels have wavelengths in the same range as the first lower reference channels, approximately 2.8 to 3.1 microns. The second upper reference channels have wavelengths in the same range as the first upper reference channels, approximately 3.8 to 4.1 microns. Second lower interference absorption signals of the plurality of second lower reference channels are determined and second upper interference absorption signals of the plurality of second upper reference channels are determined. The absorption at a first measurement channel is measured and the absorption at a second measurement channel is measured.

A first measurement interference absorption signal is extrapolated from a first linear function or relationship between the first lower interference absorption signals and the first upper interference absorption signals. The first measurement interference absorption signal is then subtracted from the first measurement absorption to determine a first true measurement channel. A second measurement interference absorption signal is extrapolated from a second linear function or relationship between the second lower interference absorption signals and the second upper interference absorption signals. The second measurement interference absorption signal is then subtracted from the second measurement absorption to determine a second true measurement channel.

It should be understood that the number of measurement channels may be limited by the size and weight constraints of a portable unit. The present invention is designed to accommodate a lightweight, inexpensive, portable unit which can effectively be used to accurately determine the presence of gases, for example natural gas.

If it is desired to confirm the presence of three types of gas, a detector would have three measurement channels and a corresponding number of lower and upper reference channels. Additionally, if there is one measurement channel, there should be at least one lower and one upper reference channel. In other words, to practice the process of this invention, a minimum of two band pass filters 18a are necessary; one of the band pass filters 18a is for the measurement channel and the second is for the reference channel. It is apparent that using only two band pass filters 18a significantly reduces the accuracy as opposed to using at least three band pass filters 18a, including an upper reference channel filter 18au and a lower reference channel filter 18al. Two band pass filters 18a provide less accuracy since the increasing difference between the lower and upper interference absorption signals cannot be accounted for by the extrapolation process.

The term "reference channel" throughout the specification and claims is used synonymously with "band pass filter 18a". Furthermore, the reference channels may comprises a plurality of upper or lower reference channels.

In another embodiment of natural gas detecting apparatus 10, according to this invention, gas concentration is process and displayed in terms of absorbance to minimize error. A representation of gas concentration is displayed by meter 30. To provide an indication of the gas type detected, processing circuits 25 of natural gas detecting apparatus 10 compute the ratio of absorbances to obtain a signal indicative of the type of hydrocarbon gas in air and which is independent of gas concentration. This information is displayed by meter 32.

Computation of the ratio of absorbances by function generating circuit 89 produces a signal which is indicative of the type or average type of hydrocarbon gas in air and largely independent of the concentration of the gas.

The absorbance signal in channel 83 is applied to logarithm circuit 91 which produces a drive signal for meter 30. Similarly the signal S, representing the ratio of absorbances produced by function circuit 89, is applied to logarithm circuit 92 which produces a drive circuit for meter 32. Use of logarithmic values of the signals compresses the drive signals for meters 30 and 32 and obviates the need for range switching. Very small values for the signal S indicate the presence primarily of methane. The value of offset factor K1, as shown in FIG. 2, is chosen to make the signal S approximately equal to zero for methane. A small addition of higher hydrocarbons (C2 to C6 or higher) increases the measured value of signal S because of the shift in absorption of these hydrocarbons towards longer wavelengths. A small scale reading at C1 is indicative of swamp gas. A near mid-scale reading near C1 but between it and C2 is indicative of natural gas. A reading at C3 above mid scale is indicative of propane. A near full scale reading at C6 is indicative of gasoline vapors.

In such embodiment, natural gas detecting apparatus 10 measures the entire concentration range of methane from 10 to $10^6$ ppm and displays the result without range switching of meters 30 and 32. FIG. 2 illustrates the results of measuring the signal S as the concentration shifted from methane to hexane and the number of carbon atoms per molecule increases from one to six, for an offset factor equal to zero, and for an offset factor equal to 0.37. Signals obtained in signal channel 84 correspond to the type of gas, rather than quantity or concentration of gas.

The alarm circuit includes a comparator circuit 95 which compares the amplitude of the signal in channel 83 with a reference value established by reference network 96 and energizes an audible alarm device 97 or a visual alarm device 98 as a function of the setting of a manually operated switch 99. Alarm circuit 33 provides an audible or visual alarm whenever the measured concentration in parts per million (ppm) surpasses an adjustable upper limit established by the reference network. This allows the operator to concentrate on the sample collecting process rather than having to monitor meters 30 and 32 continuously.

While in the foregoing specification this invention has been described in relation to certain preferred embodiments thereof, and many details have been set forth for purposes of illustration, it will be apparent to those skilled in the art that the invention is susceptible to additional embodiments and that certain of the details described herein can be varied considerably without departing from the basic principles of the invention.

I claim:

1. A method of eliminating water vapor absorption in detecting gases, the method comprising the steps of:

emitting infrared light from a light source into an optical cell;

admitting a sample gas into said optical cell;

positioning at least one reference channel band pass filter and at least one measurement channel band pass filter between said optical cell and infrared radiation detector;

passing said infrared light through said optical cell and through each said reference channel band pass filter and each said measurement channel band pass filter;

detecting filtered light emitted through each said reference channel band pass filter and each said measurement channel band pass filter;

detecting a water vapor absorption signal of the water vapor interference using a reference channel;

measuring first lower absorption signals of a plurality of first lower reference channels;

measuring first upper absorption signals of a plurality of first upper reference channels;

determining first lower interference absorption signals from the measured first lower absorption signals and corresponding stored first lower absorption signals;

determining first upper interference absorption signals from the measured first upper absorption signals and corresponding stored first upper absorption signals;

measuring second lower absorption signals of a plurality of second lower reference channels;

measuring second upper absorption signals of a plurality of second upper reference channels;

determining second lower interference absorption signals from the measured second lower absorption signals and corresponding stored second lower absorption signals;

determining second upper interference absorption signals from the measured second upper absorption signals and corresponding stored second upper absorption signals;

measuring a first measurement absorption signal of a first measurement channel;

measuring a second measurement absorption signal of a second measurement channel;

extrapolating a first measurement interference absorption signal from a first linear function between said first lower interference absorption signals and said first upper interference absorption signals;

extrapolating a second measurement interference absorption signal from a second linear function between said second lower interference absorption signals and said second upper interference absorption signals;

determining a first true measurement channel by subtracting said first measurement interference absorption signal from said first measurement absorption signal; and determining a second true measurement channel by subtracting said second measurement interference absorption signal from said second measurement absorption signal.

2. The method according to claim 1 wherein the measurement interference absorption signals are approximately equal to a composite interference signal from the lower reference channels and the upper reference channels.

3. The method according to claim 1 wherein said lower reference channels each have a lower wavelength in a range from about 2.8 to about 3.0 microns, said upper reference channels each have a wavelength in a range from about 3.8 to about 4.1 microns, and said measurement channels each have a measurement wavelength of about 3.2 microns.

4. The method according to claim 1 wherein said light source passes through 6 said band pass filters.

5. The method according to claim 1 wherein said light source passes through 12 said band pass filters.

6. The method according to claim 1 wherein each of said band pass filters occupy an area of a light chopper means.

7. The method according to claim 6 wherein said area is divided into halves and each said half is capable of holding two said band pass filters.

8. The method according to claim 6 wherein said area forms a circular section.

9. The method according to claim 1 wherein said optical cell is about 50 cm. long.

10. The method according to claim 1 wherein said optical cell has a diameter ranging from about 0.25 to about 8.0 cm.

11. The method according to claim 1 wherein said optical cell is opaque to light other than from said light source.

12. The method according to claim 1 wherein said optical cell has an inner reflective surface.

13. The method according to claim 1 wherein said infrared radiation detector has light chopper means and said infrared radiation detector controls and positions said light chopper means so that filtered light from each of said band pass filters is detected by said infrared radiation detector.

14. An improved method of detecting gaseous elements wherein a light source is directed into an optical cell, a sample gas is admitted into the optical cell, band pass filters are passed through light emitted from the light source, filtered light emitted from the band pass filters is detected in an infrared radiation detector, the sample gas is identified as a function of a wavelength of the filtered light, the improvement comprising the steps of:

detecting a water vapor absorption signal in a measurement channel;

measuring first lower absorption signals of a plurality of first lower reference channels;

measuring first upper absorption signals of a plurality of first upper reference channels;

determining first lower interference absorption signals from the measured first lower absorption signals and corresponding stored first lower absorption signals;

determining first upper interference absorption signals from the measured first upper absorption signals and corresponding stored first upper absorption signals;

measuring second lower absorption signals of a plurality of second lower reference channels;

measuring second upper absorption signals of a plurality of second upper reference channels;

determining second lower interference absorption signals from the measured second lower absorption signals and corresponding stored second lower absorption signals;

determining second upper interference absorption signals from the measured second upper absorption signals and corresponding stored second upper absorption signals;

measuring a first measurement absorption signal of a first measurement channel;

measuring a second measurement absorption signal of a second measurement channel;

extrapolating a first measurement interference absorption signal from a first linear function between said first lower interference absorption signals and said first upper interference absorption signals;

extrapolating a second measurement interference absorption signal from a second linear function between said second lower interference absorption signals and said second upper interference absorption signals;

determining a first true measurement channel by subtracting said first measurement interference absorption signal from said first measurement absorption signal; and determining a second true measurement channel by subtracting said second measurement interference absorption signal from said second measurement absorption signal.

15. A method of eliminating water vapor absorption in detecting gaseous elements, the method comprising the steps of:

passing infrared light through a gas sample;

positioning at least two band pass filters between sampling means and an infrared radiation detector;

measuring first lower absorption signals of a plurality of first lower reference channels;

measuring first upper absorption signals of a plurality of first upper reference channels;

determining first lower interference absorption signals from the measured first lower absorption signals and corresponding stored first lower absorption signals;

determining first upper interference absorption signals from the measured first upper absorption signals and corresponding stored first upper absorption signals;

measuring second lower absorption signals of a plurality of second lower reference channels;

measuring second upper absorption signals of a plurality of second upper reference channels;

determining second lower interference absorption signals from the measured second lower absorption signals and corresponding stored second lower absorption signals;

determining second upper interference absorption signals from the measured second upper absorption signals and corresponding stored second upper absorption signals;

measuring a first measurement absorption signal of a first measurement channel;

measuring a second measurement absorption signal of a second measurement channel;

extrapolating a first measurement interference absorption signal from a first linear function between said first lower interference absorption signals and said first upper interference absorption signals;

extrapolating a second measurement interference absorption signal from a second linear function between said second lower interference absorption signals and said second upper interference absorption signals;

determining a first true measurement channel by subtracting said first measurement interference absorption signal from said first measurement absorption signal; and determining a second true measurement channel by subtracting said second measurement interference absorption signal from said second measurement absorption signal.

* * * * *